(12) United States Patent
Yakobson et al.

(10) Patent No.: US 8,084,508 B2
(45) Date of Patent: Dec. 27, 2011

(54) ETHANOL AS A FEEDSTOCK FOR A BCTL FACILITY

(75) Inventors: Dennis Yakobson, Arvada, CO (US); Harold A. Wright, Longmont, CO (US); Richard Penning, Santa Monica, CA (US)

(73) Assignee: Rentech, Inc., Los Angeles, CA (US)

( * ) Notice: Subject to any disclaimer, the term of this patent is extended or adjusted under 35 U.S.C. 154(b) by 375 days.

(21) Appl. No.: 12/351,160

(22) Filed: Jan. 9, 2009

(65) Prior Publication Data

US 2009/0172996 A1    Jul. 9, 2009

Related U.S. Application Data

(60) Provisional application No. 61/019,998, filed on Jan. 9, 2008.

(51) Int. Cl.
*C07C 27/00* (2006.01)

(52) U.S. Cl. ......... 518/700; 518/702; 518/703; 518/704

(58) Field of Classification Search .................. 518/700, 518/702–704
See application file for complete search history.

(56) References Cited

U.S. PATENT DOCUMENTS

| | | | | |
|---|---|---|---|---|
| 2001/0023034 A1* | 9/2001 | Verykios | .......................... | 429/17 |
| 2005/0210739 A1* | 9/2005 | Esen et al. | ....................... | 44/605 |

FOREIGN PATENT DOCUMENTS

| | | |
|---|---|---|
| JP | 2005-105285 A | 4/2005 |
| JP | 2007-262157 A | 10/2007 |
| JP | 2007-270110 A | 10/2007 |
| WO | 2004/041716 A1 | 5/2004 |
| WO | 2007/146507 A2 | 12/2007 |

OTHER PUBLICATIONS

Morgenstern et al., Low-Temperature Reforming of Ethanol over Copper-Plated Raney Nickel, (Abstract of Energy & Fuels (2005), 19(4), 1708-1716.*
PCT/US2009/030606 International Search Report dated Jun. 30, 2009.

* cited by examiner

*Primary Examiner* — Jafar Parsa

(57) ABSTRACT

A method of producing fuel by converting an alcohol stream comprising at least one alcohol into synthesis gas; providing a first synthesis gas stream, wherein at least a portion of the first synthesis gas stream comprises synthesis gas obtained from the alcohol conversion; converting a feed comprising synthesis gas via Fischer-Tropsch into a Fischer-Tropsch product comprising hydrocarbons, wherein at least a portion of the feed comprises synthesis gas from the first synthesis gas stream; and converting at least a portion of the Fischer-Tropsch product into fuel. A diesel fuel comprising hydrocarbons formed by Fischer-Tropsch conversion of synthesis gas derived from an alcohol stream comprising at least one alcohol.

27 Claims, 3 Drawing Sheets

ETHANOL AS A FEEDSTOCK FOR A BCTL FACILITY

CROSS-REFERENCE TO RELATED APPLICATIONS

This application claims the benefit under 35 U.S.C. §119 (e) of U.S. Provisional Patent Application Ser. No. 61/019,998 filed Jan. 9, 2008, which is hereby incorporated herein by reference in its entirety.

STATEMENT REGARDING FEDERALLY SPONSORED RESEARCH OR DEVELOPMENT

Not Applicable.

BACKGROUND

1. Field of Technology

The present invention generally relates to processes for producing fuel. More specifically, the invention relates to the production of fuel using alcohol derived from any source as a feedstock or co-feedstock with coal, biomass, petcoke, or natural gas in a synthesis gas refinery.

2. Background of the Invention

It is well known that internal combustion engines have revolutionized transportation following the invention thereof during the last decades of the 19th century. While others, including Karl Benz and Gottleib Wilhelm Daimler, invented and developed engines using electric ignition of fuel such as gasoline, Rudolf C. K. Diesel invented and built the engine named for him which employs compression for auto-ignition of the fuel, enabling utilization of low-cost organic fuels. Modern high performance diesel engines require increasingly advanced fuel compositions.

Currently, the majority of fuels for transportation are derived from natural petroleum. Petroleum remains the world's main source of hydrocarbons used as fuel and petrochemical feedstock. While compositions of natural petroleum or crude oils are significantly varied, all crude contains sulfur compounds and most crude contains nitrogen compounds which may also contain oxygen, but the oxygen content of most crude is low.

Fuels such as diesel which are used widely in automotive transport and for providing power for heavy duty equipment are of great interest due to their high fuel economy. However, one of the problems with diesel fuels is that, when such fuels are burned in internal combustion engines, pollutants in the exhaust gases are emitted into the environment. Some of the most common pollutants in diesel exhausts are nitric oxide and nitrogen dioxide (hereafter abbreviated as "NOx"), hydrocarbons and sulfur dioxide, and to a lesser extent carbon monoxide. In addition, diesel powered engines also generate a significant amount of particulate emissions (PM) which include soot, adsorbed hydrocarbons, and sulfates, which are usually formed due to the incomplete combustion of the fuel and cause of dense black smoke emitted by such engines through the exhaust.

Crude oil is seldom used as produced at the well, but is converted in oil refineries into a wide range of fuels and petrochemical feedstocks. Fuels for transportation are typically produced by processing and blending distilled fractions from the crude to meet particular end use specifications. Because most of the crude available today in large quantity is high in sulfur, the distilled fractions must be desulfurized to yield products which meet performance specifications and/or environmental standards. As mentioned above, sulfur-containing organic compounds in fuels continue to be a major source of environmental pollution. During combustion they are converted to sulfur oxides which, in turn, give rise to sulfur oxyacids and also contribute to particulate emissions.

Distilled fractions used for fuel or a blending component of fuel for use in compression ignition internal combustion engines (diesel engines) are middle distillates that usually contain from about 1 to 3 percent by weight sulfur. In the past a typical specifications for diesel fuel was a maximum of 0.5 percent by weight. By 1993 legislation in Europe and United States limited sulfur in diesel fuel to 0.3 weight percent. By 1996 in Europe and United States, and 1997 in Japan, maximum sulfur in diesel fuel was reduced to no more than 0.05 weight percent. This world-wide trend must be expected to continue to even lower levels for sulfur.

Introduction of new emission regulations has prompted significant interest in catalytic exhaust treatment. Challenges of applying catalytic emission control for the diesel engine, particularly the heavy-duty diesel engine, are significantly different from the spark ignition internal combustion engine (gasoline engine) due to two factors. First, the conventional three way catalyst (TWC) is ineffective in removing $NO_x$ emissions from diesel engines, and second, the need for particulate control is significantly higher than with the gasoline engine.

Several exhaust treatment technologies are emerging for control of diesel engine emissions, and in all sectors the level of sulfur in the fuel affects efficiency of the technology. Sulfur is a catalyst poison that reduces the activity of catalysts. High fuel sulfur also creates a secondary problem of particulate emission during catalytic control of diesel emissions, due to catalytic oxidation of sulfur and reaction with water to form a sulfate mist. This mist is collected as a portion of particulate emissions. While an increase in combustion temperature can reduce particulate, this leads to an increase in NOx emission by the well-known Zeldovitch mechanism. Thus, it becomes necessary to trade off particulate and NOx emissions to meet emissions legislation.

Available evidence strongly suggests that ultra-low sulfur diesel (ULSD) is a significant technology enabler for catalytic treatment of diesel exhaust to control emissions. Fuel sulfur levels of below 15 ppm are likely required to achieve particulate levels below 0.01 g/bhp-hr. Such levels would be compatible with catalyst combinations for exhaust treatment now emerging, which have shown capability to achieve NOx emissions around 0.5 g/bhp-hr. Furthermore, NOx trap systems are extremely sensitive to fuel sulfur and available evidence suggests that they need sulfur levels below 10 ppm to remain active.

Conventional hydrodesulfurization (HDS) catalysts can be used to remove a major portion of the sulfur from petroleum distillates for the blending of refinery transportation fuels, but they are not efficient for removing sulfur from compounds where the sulfur atom is sterically hindered, as in multi-ring aromatic sulfur compounds. This is especially true where the sulfur heteroatom is doubly hindered (e.g., 4,6-dimethyldibenzothiophene). Using conventional hydrodesulfurization catalysts at high temperatures would cause yield loss, faster catalyst coking, and product quality deterioration (e.g., color). High pressure utilization also incurs a large capital outlay.

In order to meet strict specifications, hindered sulfur compounds will also have to be removed from distillate feedstocks and products. There is a pressing need for economical removal of sulfur from distillates and other hydrocarbon products and the art provides many processes said to remove sulfur from distillate feedstocks and products. These methods have been of limited utility, however, since only a rather low degree of desulfurization is achieved. Also, substantial loss of valuable products may result due to cracking and/or coke formation during the utilization of these methods.

As described in U.S. Pat. No. 6,824,574 to O'Rear, et al., the increased demand for middle distillate transportation fuels such as jet fuel and diesel fuel has provided the incentive for expanding the production of these fuels by converting natural gas, coal and heavy petroleum fractions. The growing importance of alternative energy sources has thus brought a renewed interest in Fischer-Tropsch synthesis as one of the more attractive direct and environmentally acceptable paths to high quality transportation fuels, as Fischer-Tropsch synthesis may be used to create Fischer-Tropsch diesel comprising very low levels or substantially no sulfur.

The Fischer-Tropsch synthesis for processing these resources into distillate fuels involves a Fischer-Tropsch reaction whereby synthesis gas containing essentially hydrogen and carbon monoxide is converted into highly linear hydrocarbonaceous products containing paraffins, olefins and oxygenates such as acids and alcohols. The linear paraffins are converted into isoparaffinic distillate fuel components using known Fischer-Tropsch product upgrading procedures such as hydrotreating, hydrocracking and hydroisomerization dewaxing. The isoparaffinic distillate fuels have excellent burning properties, including high jet smoke points and high diesel cetane numbers.

Even in newer, high performance diesel engines, combustion of conventional fuel produces smoke in the exhaust. Oxygenated compounds and compounds containing few or no carbon-to-carbon chemical bonds, such as methanol and dimethyl ether, are known to reduce smoke and engine exhaust emissions. However, most such compounds have high vapor pressure and/or are nearly insoluble in diesel fuel, and they have poor ignition quality, as indicated by their cetane numbers. Furthermore, other methods of improving diesel fuels by chemical hydrogenation to reduce their sulfur and aromatics contents, also cause a reduction in fuel lubricity. Diesel fuels of low lubricity may cause excessive wear of fuel injectors and other moving parts which come in contact with the fuel under high pressures.

Much current work has concentrated on the production of ethanol, which has been viewed as a final fuel or a fuel blending component suitable for enhancing environmentally-friendliness of fuels and favorably altering the fuels, e.g. to reduce the smoke point and/or emissions. For example, as described in U.S. Pat. No. 7,208,022 to Corkwell, et al., using ethanol in gasoline is well established around the world. Mixing alcohol, e.g. ethanol, with diesel has proven problematic due to the phase separation which occurs, leading to corrosion, etc., and the need for emulsions. Indeed, ethanol-diesel fuel mixtures have suffered in a variety of performance areas: stability (especially in the presence of water), corrosion, reduced power, lubricity, and low temperature properties. Ethanol-diesel fuel mixtures, especially in the presence of water and/or low temperatures, tend to be unstable resulting in separation to polar and nonpolar phases. The corrosive properties of ethanol have been assigned to the instability of the mixture when exposed to contaminant water in the fuel delivery system. Thus, while the use of ethanol in diesel fuel systems can offer economic and environmental advantages from a renewable fuel point of view, the presence of water presents complex technical problems relating to storage and use of such fuels.

As methods of producing ethanol and other mixed alcohols from various readily-available sources prove increasingly economical, methods of producing suitable fuels therefrom are needed. Accordingly, there is a need in the art for a method of producing environmentally-friendly fuels from alcohols. The fuel desirably has a low sulfur content leading to a relative ease of removing particulate matter (PM) upon combustion, e.g. via catalytic conversion. Such a fuel may desirably be used alone or blended with other fuels or fuel components.

SUMMARY

Herein provided is a method of producing fuel, the method comprising: converting an alcohol stream comprising at least one alcohol into synthesis gas; providing a first synthesis gas stream, wherein at least a portion of the first synthesis gas stream comprises synthesis gas obtained from the alcohol conversion; converting a feed stream comprising synthesis gas via Fischer-Tropsch into Fischer-Tropsch product comprising hydrocarbons, wherein at least a portion of the feed comprises synthesis gas from the first synthesis gas stream; and converting at least a portion of the Fischer-Tropsch product into fuel. The at least one alcohol may comprise ethanol. The at least one alcohol may be derived from corn, sugar cane, biomass, lignocellulose, cellulose, coal, natural gas, or a combination thereof. In embodiments, ethanol is derived from lignocellulose, cellulose, or a combination thereof. In some embodiments, at least a portion of the ethanol is derived from fermentation of sugar cane, fermentation of corn, thermochemical conversion of synthesis gas or a combination thereof.

In some embodiments of the method of producing fuel, converting an alcohol stream comprising at least one alcohol into synthesis gas comprises converting ethanol to synthesis gas by reforming, partial oxidation, gasification, or a combination thereof. In some embodiments, the first synthesis gas stream further comprises synthesis gas obtained from at least one process selected from gasification of coal, gasification of biomass, reforming of natural gas, and combinations thereof.

In embodiments, the at least one alcohol is ethanol and converting the alcohol stream into synthesis gas comprises gasifying the alcohol stream to produce a gasifier product comprising synthesis gas having a first $H_2$:CO ratio. In some embodiments, the method comprises combining the gasifier product with additional synthesis gas to yield the first synthesis gas stream, wherein the first synthesis gas stream has a second $H_2$:CO ratio. The second $H_2$:CO ratio may be greater than the first $H_2$:CO ratio. Alternatively, the second $H_2$:CO ratio may be less than the first $H_2$:CO ratio The additional synthesis gas may be obtained from at least one process selected from gasification of coal, gasification of biomass, reforming of natural gas, and combinations thereof. The method may further comprise gasifying at least one selected from liquid hydrocarbons, coal, biomass, petcoke and combinations thereof.

The method may further comprise shifting the gasifier product via water gas shift reaction, whereby water and a portion of the carbon monoxide in the gasifier product are converted into additional hydrogen and carbon dioxide, whereby a water gas shift product having a second $H_2$:CO ratio is obtained, wherein the second $H_2$:CO ratio is greater than the first $H_2$:CO ratio.

In embodiments, the at least one alcohol comprises ethanol and converting the alcohol stream into synthesis gas comprises reforming the alcohol stream. Reforming may comprise autothermal reforming. The method may further comprise reforming of natural gas.

The method may further comprise removing at least one component from the first synthesis gas stream. The at least one component may be selected from the group consisting of sulfur, carbon dioxide, halides, sulfur-containing compounds, hydrogen, and combinations thereof. In embodiments, the at least one component is hydrogen and converting at least a portion of the Fischer-Tropsch product into fuel comprises upgrading at least a portion of the Fischer-Tropsch product via hydrogenation, wherein at least a portion of the removed hydrogen is utilized to hydrogenate the Fischer-Tropsch product.

In embodiments, the fuel is selected from aviation-grade fuels, aviation-grade fuel components, diesel fuels, diesel fuel components, and combinations thereof. In embodiments, the fuel has a sulfur level less than that of ULSD. For example, in embodiments, the fuel comprises less than 1 ppm sulfur.

In certain embodiments, upon combustion, the fuel produces NOx emissions at a level at least as low as that of ultra low sulfur diesel, ULSD. For example, in embodiments the fuel produces less than 1 g/tonne-kg NOx. In certain embodiments, upon combustion, the fuel produces PM10 at least as low as that of ULSD. For example, in embodiments, upon combustion, the fuel produces less than about 40 mg/tonne-km of particulate matter, PM10. The fuel produced via the disclosed method may have a cetane number of greater than about 40.

Also disclosed via this disclosure is a fuel produced according to the method provided. A diesel fuel comprising hydrocarbons, is described herein, the diesel fuel formed by Fischer-Tropsch conversion of synthesis gas derived from an alcohol stream comprising at least one alcohol. The synthesis gas produced from an alcohol stream comprising at least one alcohol may be converted into hydrocarbons by Fischer-Tropsch reaction. In embodiments, the fuel comprises C12-C20 hydrocarbons. In some embodiments, at least a portion of the synthesis gas from which the diesel fuel is produced is derived from the reforming of ethanol. In embodiments, at least a portion of synthesis gas from which the fuel is produced is derived from gasification of ethanol.

Thus, embodiments described herein comprise a combination of features and advantages intended to address various shortcomings associated with certain prior systems and methods. The various characteristics described above, as well as other features, will be readily apparent to those skilled in the art upon reading the following detailed description of the preferred embodiments, and by referring to the accompanying drawings.

BRIEF DESCRIPTION OF THE DRAWINGS

For a more detailed description of the present invention, reference will now be made to the accompanying drawings, wherein.

In the Figures, like numbers are utilized to refer to similar components.

NOTATION AND NOMENCLATURE

In the following discussion and in the claims, the terms "comprising," "including" and "containing" are used in an open-ended fashion, and thus should be interpreted to mean "including, but not limited to . . . ".

The singular forms "a," "an," and "the" include plural referents unless the context clearly dictates otherwise.

The term "about," when used in the context of a numerical value, means approximately or reasonably close to the given number, and generally includes, but is not limited to, ±10% of the stated number.

DETAILED DESCRIPTION

Overview

Ethanol and other mixed alcohols can be produced from many sources. These alcohols can typically be used directly as fuels in many applications. However, as mentioned hereinabove, in circumstances where ethanol or alcohols cannot be used as fuel, e.g. heavy duty trucks and jet aircraft, there is a need to convert the ethanol or mixed alcohols to diesel or jet fuel. The method of this disclosure may be utilized to achieve this goal.

Improvements in the efficiency of alcohol production, e.g. ethanol production, may lead to low cost alcohol to rival coal and other feed stocks in cost. However, as ethanol cannot be used as a neat fuel in many transportation vehicles, there may arise an economic incentive to convert alcohol, e.g. ethanol, to diesel and/or jet fuel for heavy truck and aviation use. Rather than using alcohol as a neat fuel or as an additive to diesel fuels, which can vary significantly in their compositions, alcohols are converted to environmentally-friendly fuels or fuel blending components via the method and system of this disclosure. Using the system and method of this disclosure, alcohol is converted into environmentally-friendly fuel and/or fuel components by converting the alcohol to synthesis gas and subsequently converting at least a portion of the alcohol-derived synthesis gas into a fuel via Fischer-Tropsch.

Process Description

Figure 1:
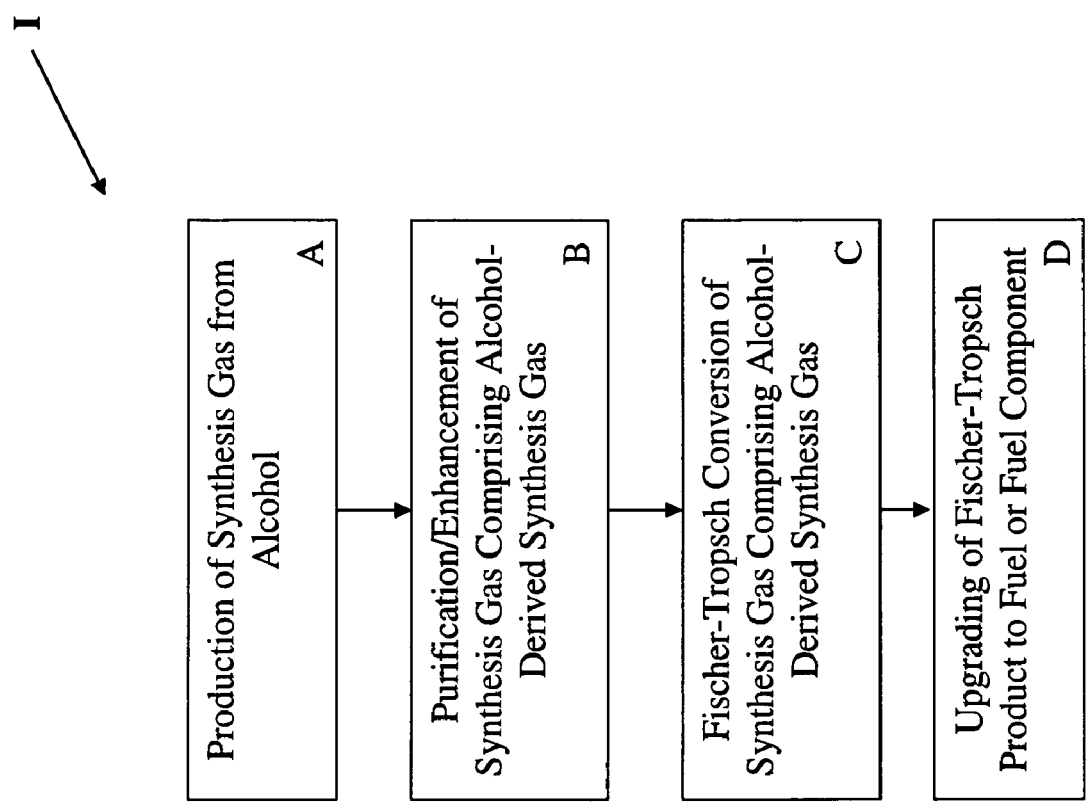
FIG. 1 is a flow diagram of a process according to this invention.

FIG. 1 is a flow diagram of a process I according to this disclosure. At step A, synthesis gas is produced from alcohol. The alcohol from which the synthesis gas is produced may comprise ethanol. The synthesis gas may be produced by reforming, partial oxidation, gasification, or any other methods or combination of methods known in the art to be suitable for converting alcohol to synthesis gas. As will be discussed further hereinbelow, the alcohol may be converted to synthesis in the presence of one or more additional feed material, such as, but not limited to, biomass, coal and natural gas.

At step B, synthesis gas comprising alcohol-derived synthesis gas is purified or otherwise enhanced. In some embodiments, step B may be absent from process I. Purifying the synthesis gas may comprise removing a contaminant from the synthesis gas. For example, carbon dioxide, sulfur, sulfur-containing compounds, halides, or a combination thereof may be removed from the synthesis gas by any means known to one of skill in the art. In applications, acid gas removal may be used to remove carbon dioxide and hydrogen sulfide from the synthesis gas. In applications, enhancement comprises removal of hydrogen from the synthesis gas to adjust the $H_2$:CO ratio to a desired range for downstream Fischer-Tropsch (FT). In applications, enhancement comprises subjecting the synthesis gas to water gas shift removal, whereby water (steam) is reacted with the carbon monoxide in the synthesis gas to produce additional hydrogen and carbon dioxide. Following water-gas shift reaction, a portion of the hydrogen may be removed from the shifted synthesis gas, for example, via hydrogen membrane technology. In embodiments, purification/enhancement comprises any combination of two or more of contaminant removal, water-gas shift and hydrogen removal. The synthesis gas that is purified and/or otherwise enhanced in step B comprises alcohol-derived synthesis gas and may further comprise synthesis gas derived from another feed source.

At step C, synthesis gas comprising at least some portion of the alcohol-derived synthesis gas produced in step A is converted via Fischer-Tropsch into higher hydrocarbons. The synthesis gas may be converted via introduction into one or more Fischer-Tropsch reactors comprising Fischer-Tropsch catalyst. Converting the synthesis gas via Fischer-Tropsch may be performed as known in the art and further discussed hereinbelow.

Following Fischer-Tropsch conversion, the Fischer-Tropsch product is upgraded at step D into suitable low-sulfur fuel or fuel-blending components. Upgrading may comprise separation of the Fischer-Tropsch products into desirable boiling point fractions, blending of fractions, isomerization, hydrogenation, addition of property-enhancing components, or a combination thereof. The fuel produced via the disclosed system and method may be jet-grade aviation fuel, an aviation-grade fuel component, diesel fuel, a diesel fuel component, or a combination thereof.

A more detailed description of the process of this disclosure will be made with reference to FIG. 2, which is a schematic of a fuel production system 10 suitable for carrying out a process for producing fuel (or fuel additive) from alcohol-derived synthesis gas according to an embodiment of this disclosure. Fuel production system 10 comprises synthesis gas production unit 15, purification/enhancement unit 25, Fischer-Tropsch reactor 50, and product upgrading unit 80.

A. Production of Synthesis Gas from Alcohol

The fuel production method comprises producing synthesis gas from alcohol. As indicated in FIG. 2, an alcohol feed comprising at least one alcohol is introduced via alcohol inlet line 5 into synthesis gas production unit 15, wherein synthesis gas is produced therefrom. In embodiments, the at least one alcohol comprises ethanol.

The most common source of ethanol in the U.S. is the fermentation of corn sugars. In Brazil, low cost ethanol is produced from fermentation of sugar cane. However, use of cellulosic or ligno-cellulosic materials is becoming economically and environmentally desirable, and in embodiments, the alcohol feed is derived from cellulose or lignocellulose.

Ethanol has several advantages over fossil-fuel derived materials (e.g., methane, methanol) as a source for synthesis gas. Ethanol represents a renewable and $CO_2$-neutral source that can be readily obtained from fermentation of biomass. The use of ethanol appears even more economically favorable when one considers the likely increases in the prices of petroleum and other fossil fuels due to depletion of world reserves. Ethanol may be a particularly attractive energy and synthesis gas source for countries that lack fossil fuel resources, but have significant agricultural economy. As a result of advances in biotechnology, virtually any biomass can now be converted into ethanol.

The alcohol fed into synthesis gas production unit 15 via line 5 may be derived from any available source. In embodiments, the alcohol feed is derived from corn, sugar cane, biomass, lignocellulose, cellulose, coal, natural gas, or a combination thereof. In applications, the alcohol feed comprises ethanol and optionally other alcohols produced from low cost cellulosic material. In embodiments, the alcohol feed comprises ethanol derived from lignocellulose, cellulose, or a combination thereof, as such sources of ethanol may be economically desirable. In embodiments, the alcohol feed comprises low cost ethanol produced from cellulosic materials and/or from sugar cane fermentation. In other embodiments, the ethanol is produced via thermochemical conversion from synthesis gas. In embodiments, the alcohol feed is derived from fermentation of corn. In embodiments, at least a portion of the alcohol feed is derived from fermentation of sugar cane, fermentation of corn, thermochemical conversion of synthesis gas or a combination thereof.

The alcohol feed is converted into synthesis gas via any known methods, and synthesis gas production unit 15 may comprise any unit capable of converting the alcohol in the alcohol fed thereto via alcohol inlet line 5 into synthesis gas. In embodiments, synthesis gas is produced in synthesis gas production unit 15 from the alcohol by reforming, partial oxidation, gasification, or a combination thereof. Alcohol-derived synthesis gas produced in synthesis gas production unit 15 is extracted from synthesis gas production unit 15 via line 20.

In embodiments, synthesis gas production unit 15 comprises a gasifier. In such embodiments, alcohol feed may be co-fed into synthesis gas production unit 15 with a co-feed introduced via co-feed inlet line 7. The co-feed comprises additional carbonaceous material from which synthesis gas may be derived. The co-feed may be one or more selected from coal, biomass, petcoke, and liquid hydrocarbons. In other applications, the alcohol and the co-feed stream are combined prior to introduction via a single inlet line into a gasifier. Thus, in embodiments, the alcohol-derived synthesis gas in line 20 comprises, in addition to alcohol-derived synthesis gas, synthesis gas derived from at least one process selected from gasification of coal, gasification of biomass and reforming of natural gas.

In embodiments, synthesis gas production unit 15 is a gasifier, and converting alcohol into alcohol-derived synthesis gas comprises introducing a gasifier feedstream comprising ethanol into a gasifier to produce a gasifier product comprising alcohol-derived synthesis gas having a first $H_2$:CO ratio. The gasifier feedstream may further comprise at least one selected from liquid hydrocarbons, coal, biomass, and petcoke or may be co-fed via inlet line 7 at least one selected from liquid hydrocarbons, coal, biomass, petcoke and combinations thereof.

Synthesis gas production unit 15 may be a reformer. In such embodiments, water/steam (with or without oxygen) may be introduced into the reformer along with the alcohol feed. Water/steam (with or without oxygen) may be introduced via inlet line 7. In embodiments, synthesis gas production unit 15 is an autothermal reformer. In embodiments, the alcohol feed comprises natural gas in addition to the at least one alcohol. In embodiments, the alcohol feed is co-fed to the reformer with natural gas to yield alcohol-derived synthesis gas.

In embodiments, converting alcohol into synthesis gas comprises introducing a reformer feed comprising ethanol into a reformer. The reformer may be an autothermal reformer. The reformer feed may comprise natural gas in addition to ethanol. In embodiments, the ethanol or mixed alcohol reformer feed is reformed with water/steam (with or without $O_2$) to synthesis gas. Reforming of ethanol may occur at temperatures in the range 300° C.-600° C., which is significantly lower than temperatures required for $CH_4$ or gasoline reforming.

In embodiments, converting alcohol into synthesis gas comprises steam reforming of ethanol according to any method known to those of skill in the art. For example, a variety of oxide support materials and metals have been considered for the steam reforming of ethanol. In embodiments, ethanol is steam reformed over a Ni based catalyst comprising Cu, Cr, Zn or K. In other embodiments, ethanol is reformed over a cobalt catalyst supported on ZnO. In embodiments, a dopant, such as an alkali metal, is utilized to suppress coke formation.

B. Purification of Synthesis Gas Comprising Alcohol-Derived Synthesis Gas

In embodiments, the method further comprises purifying and/or enhancing synthesis gas comprising alcohol-derived synthesis gas. Purifying may comprise removing at least one component from the alcohol-derived synthesis gas. For example, as indicated in FIG. 2, alcohol-derived synthesis gas is introduced via line 20 into one or more purification/enhancement units 25. Although indicated as a single unit in FIG. 2, two or more purification/enhancement units may be utilized. Purification enhancement unit(s) 25 may be selected from acid gas removal units, water-gas shift reactors, hydrogen separation units, carbon beds, zinc oxide beds, and combinations thereof.

Within purification/enhancement unit 25, a contaminant may be removed from the synthesis gas, for example, via line 30. In embodiments, the contaminant removed is selected from sulfur, sulfur-containing compounds, carbon dioxide, and halides. The purification/enhancement unit 25 may utilize current technology including, but not limited to, carbon beds, zinc oxide beds, etc., to remove impurities down to, for example, less than 1 ppm S and/or less than 1 ppm halides. The purification/enhancement unit may be an acid gas removal or AGR unit, and hydrogen sulfide and carbon dioxide may be removed via component removal line(s) 30.

Within purification/enhancement unit 25, synthesis gas may be enhanced. For example, purification/enhancement may comprise enhancing the synthesis gas by altering the $H_2:CO$ ratio of the synthesis gas. In such instances, purification/enhancement unit 25 may be a hydrogen separation unit, a water gas shift unit, or both. Enhancing the synthesis gas may comprise removing hydrogen from the alcohol-derived synthesis gas. In such instances, purification/enhancement unit 25 may comprise a hydrogen membrane unit. In this manner, the $H_2:CO$ ratio of the synthesis gas may be reduced prior to introduction into FT reactor 50. In applications, enhancing the synthesis gas comprises shifting the synthesis gas in a water gas shift, WGS, reactor such that steam and carbon monoxide are converted into additional hydrogen and carbon dioxide. The $H_2:CO$ ratio exiting the WGS purification/enhancement unit 25 may be greater than the $H_2:CO$ ratio of the synthesis gas fed into the WGS unit. Enhancing the synthesis gas may comprise shifting the alcohol-derived synthesis gas and subsequently removing hydrogen from the shifted synthesis gas. Via shifting and/or hydrogen removal, the $H_2:CO$ ratio of the synthesis gas provided to the Fischer-Tropsch reactor may be adjusted as desired.

Modified synthesis gas is removed from purification/enhancement unit(s) 25 via modified synthesis gas outlet line 40. The $H_2:CO$ ratio of the modified synthesis gas may be greater than, less than, or substantially the same as the synthesis gas fed to purification/enhancement unit(s) 25. For example, in embodiments, synthesis gas production unit 15 is a gasifier. The gasifier product, alcohol-derived synthesis gas in line 20, may have a first $H_2:CO$ ratio and may be introduced into a WGS reactor (purification/enhancement unit 25) whereby water and a portion of the carbon monoxide in the gasifier product are converted into a shifted synthesis gas product comprising additional hydrogen and carbon dioxide. The WGS outlet stream in line 40 has a second $H_2:CO$ ratio that is different from the first $H_2:CO$ ratio. In embodiments, the second $H_2:CO$ ratio is greater than the first $H_2:CO$ ratio. The WGS outlet may introduce shifted synthesis gas into a second purification/enhancement unit 25, which may be a hydrogen separation unit. Within the second purification/enhancement unit 25, hydrogen may be removed from the synthesis gas, reducing the $H_2:CO$ ratio relative to the synthesis gas fed thereto.

Synthesis gas not produced within synthesis gas production unit 15 may be combined with the alcohol-derived synthesis gas to provide a syngas feed for Fischer-Tropsch conversion. For example, a second stream of synthesis gas may be combined with modified synthesis gas in line 40 by introduction via additional synthesis gas inlet line 35. Alternatively or additionally, additional synthesis gas may be introduced upstream of purification/enhancement unit(s) 25 and purified and/or enhanced in the same manner as the alcohol-derived synthesis gas. The additional synthesis gas may be derived from a non-alcohol carbonaceous material. In embodiments, additional synthesis gas is obtained from at least one process selected from gasification of coal, gasification of biomass, reforming of natural gas, and combinations thereof. In embodiments, alcohol-derived synthesis gas having a first $H_2:CO$ ratio is combined with additional synthesis gas to yield a combination syngas stream having a second $H_2:CO$ ratio. In embodiments, the second $H_2:CO$ ratio is greater than the first $H_2:CO$ ratio. In other embodiments, the second $H_2:CO$ ratio is less than the first $H_2:CO$ ratio. In other embodiments, the second $H_2:CO$ ratio is substantially the same as the first $H_2:CO$ ratio.

Figure 3:
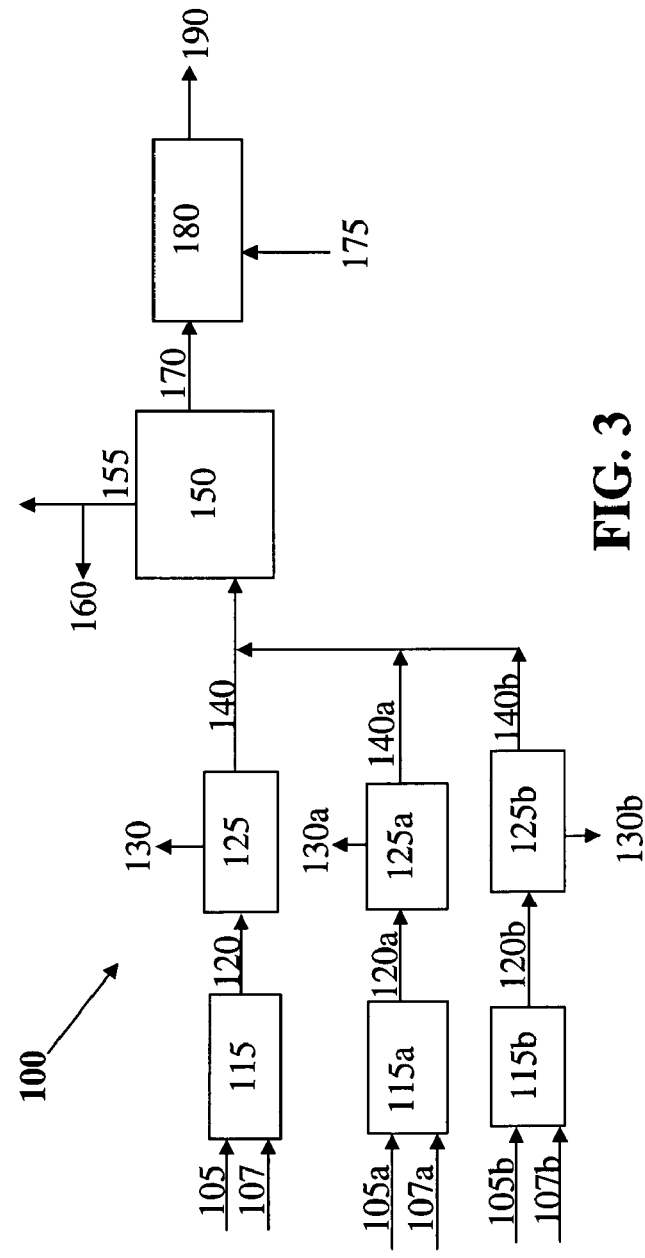
FIG. 3 is a schematic of another suitable system for carrying out a process for the production of Fischer-Tropsch fuel from alcohol-derived synthesis gas according to another embodiment of this invention.

The additional synthesis gas may be produced by one or more additional synthesis gas production units. FIG. 3 is a schematic of another suitable system 100 for carrying out a process for the production of Fischer-Tropsch fuel from alcohol-derived synthesis gas according to another embodiment of this invention. In this embodiment, two additional synthesis gas production units 115a and 115b are utilized to produce additional synthesis gas.

In the embodiment of FIG. 3, alcohol feed comprising at least one alcohol is fed into synthesis gas production unit 115 via alcohol inlet line 105. A co-feed may be introduced via co-feed line 107. Within synthesis gas production unit 115, alcohol is converted to alcohol-derived synthesis gas, as in the embodiment of FIG. 2.

In the embodiment of FIG. 3, a second synthesis gas production unit 115a and a third synthesis gas production unit 115b are employed to provide additional synthesis gas for downstream Fischer-Tropsch conversion. Additional synthesis gas production units 115a and 115b are selected from reformers, gasifiers and autothermal reformers. In embodiments, additional synthesis gas production unit 115a is a natural gas reformer. Natural gas reformer 115a may be used to convert a natural gas stream comprising methane and introduced via line 105a and oxidizing fluid comprising steam and/or oxygen introduced via line 107a into natural gas reformer product comprising synthesis gas. The reformed product comprising synthesis gas may be removed from natural gas reformer 115a via line 120a. Additional synthesis gas production unit 115b may be a gasifier. Gasifier 115b may be utilized to convert gasifier feed comprising coal, biomass, or liquid hydrocarbons introduced via line 105b into a gasifier product comprising synthesis gas. The gasifier product comprising synthesis gas may be removed from gasifier 115b via line 120b.

Figure 4:
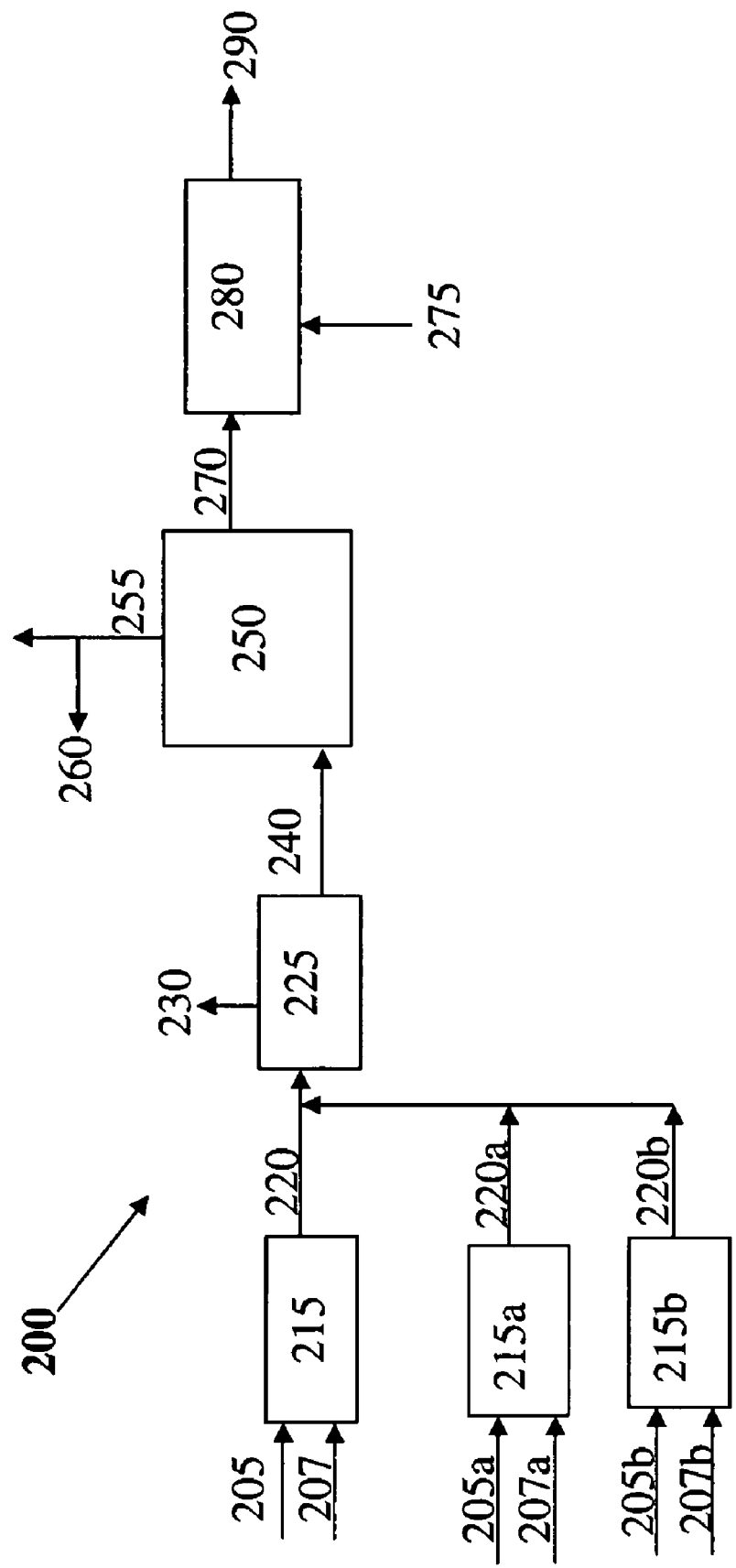
FIG. 4 is a schematic of another suitable system for carrying out a process for the production of Fischer-Tropsch fuel from alcohol-derived synthesis gas according to another embodiment of this invention.

Natural gas reformer product comprising synthesis gas and gasifier product comprising synthesis gas may be combined with alcohol-derived synthesis gas to provide a synthesis gas feed to be converted to hydrocarbons via Fischer-Tropsch. The various synthesis gas streams may be combined prior to or following purification/enhancement. In the embodiment of FIG. 3, for example, dedicated purification/enhancement units 125a and 125b are utilized to provide modified synthesis gas in lines 140a and 140b. The synthesis gas in lines 120a and 120b may be purified and/or enhanced via one or more purification/enhancement units 125a, 125b respectively in the same manner as described hereinabove in relation to purification/enhancement of alcohol-derived synthesis gas via purification/enhancement unit 25. In the embodiment of FIG. 3, the modified synthesis gas in lines 140, 140a and 140b are combined as feed to FT reactor 50. Alternatively, as shown in FIG. 4, which is a schematic of another suitable system 200 for carrying out the process for the production of Fischer-Tropsch fuel from alcohol-derived synthesis gas according to another embodiment of this invention, a single purification/enhancement unit 225 may be utilized to purify and/or enhance the synthesis gas produced in multiple synthesis gas production units. In FIG. 4, a single unit or train of units 225 is utilized to purify and/or enhance the synthesis gas produced in synthesis gas production units 215, 215a, and 215b, providing modified/enhanced synthesis gas in modified synthesis gas outlet line 240. The alcohol-derived synthesis gas in line 220 is introduced into the same unit or train of purification/enhancement units 225 as the synthesis gas in lines 220a and 220b. As for purification/enhancement unit 25, purification/enhancement units 125, 125a, 125b, and 225 may be selected from contaminant removal units (e.g., carbon dioxide removal units, sulfur removal units, sulfur-compound removal units, and halide removal units) and $H_2$:CO adjustment units (e.g., hydrogen separation units and WGS units). Removed components may be extracted from purification/enhancements 125, 125a, 125b, and 225 via one or more lines 130, 130a, 130b, and 230 respectively.

C. Fischer-Tropsch Conversion of Synthesis Gas Comprising Alcohol-Derived Synthesis Gas The disclosed fuel production method further comprises converting a synthesis gas feed, at least a portion of which is derived from alcohol, into higher hydrocarbons via Fischer-Tropsch. Synthesis gas feed comprising synthesis gas derived from alcohol is introduced into one or more Fischer-Tropsch reactor. In the embodiment of FIG. 2, synthesis gas feed in line 40 comprising synthesis gas derived from alcohol is introduced into Fischer-Tropsch reactor 50. Within the Fischer-Tropsch reactor 50, the synthesis gas is converted into Fischer-Tropsch product comprising liquid hydrocarbons and waxes. Similarly, in the embodiment of FIG. 3, synthesis gas feed comprising synthesis gas derived from alcohol is introduced via inlet line 140 into Fischer-Tropsch reactor 150. Similarly, in the embodiment of FIG. 4, synthesis gas feed comprising synthesis gas derived from alcohol is introduced via inlet line 240 into Fischer-Tropsch reactor 250.

The Fischer-Tropsch reactor(s) may be designed as slurry bubble columns. The Fischer-Tropsch reactor may be operated as known to those of skill in the art to produce Fischer-Tropsch liquid hydrocarbons and waxes from synthesis gas. In embodiments, iron catalyst is utilized to catalyze the Fischer-Tropsch conversion. Suitable Fischer-Tropsch catalyst is disclosed in, for example, U.S. Pat. No. 5,504,118, which is hereby incorporated herein in its entirety. Alternatively, the Fischer-Tropsch conversion is catalyzed by cobalt-containing catalyst, supported ruthenium-promoted cobalt catalyst, and/or cobalt-thoria-MgO catalyst on an alumina or kieselguhr support.

Tail gas comprising light product and unreacted gases is removed from FT reactor 50 (150 in FIG. 3; 250 in FIG. 4) via tailgas removal line 55 (155 in FIG. 3; 255 in FIG. 4). A portion of the tail gas may be recycled, for example, via recycle line 60 (160 in FIG. 3; 260 in FIG. 4) to reduce carbon monoxide requirements within a synthesis gas production unit (e.g., a gasifier) 15.

D. Upgrading of FT Product to Low-Sulfur Fuel or Low-Sulfur Fuel Component

The fuel production method further comprises upgrading the Fischer-Tropsch product to provide a low-sulfur fuel or fuel component. Fischer-Tropsch liquid and/or wax product is introduced into one or more product upgrading units. For example, in the embodiment of FIG. 2, Fischer-Tropsch product is introduced via FT product line 70 (170 in FIG. 3; 270 in FIG. 4) into a product upgrading unit 80 (180 in FIG. 3; 280 in FIG. 4). Although shown as single units 80, 180, 280 in the Figures, upgrading may comprise a series of units.

Product upgrading may comprise hydrogenation, isomerization, separation, blending of various separated fractions, addition of one or more property-altering components, or a combination thereof. Any method known in the art may be used to upgrade the Fischer-Tropsch product. For example, upgrading may provide middle distillate fuels, specifically jet fuels and diesel fuels, having acceptable lubricity, seal swell and density. Upgraded fuel or fuel blending component(s) is removed from the product upgrading unit(s) by product fuel line 90 (190 in FIG. 3; 290 in FIG. 4). The upgraded fuel is selected from aviation-grade fuels, aviation-grade fuel components, diesel fuels and diesel-fuel components.

In embodiments, converting at least a portion of the Fischer-Tropsch product into fuel comprises upgrading at least a portion of the Fischer-Tropsch product via hydrogenation. In embodiments, hydrogen is introduced into product upgrading unit(s) 80 (180 in FIG. 3; 280 in FIG. 4) via hydrogen inlet line 75 (175 in FIG. 3; 275 in FIG. 4). In applications, hydrogen utilized for upgrading is obtained upstream of the product upgrading unit(s) 80 (180; 280). In embodiments, at least a portion of the hydrogen for product upgrading is obtained from a purification/enhancement unit 25 (125, 125a and/or 125b in FIG. 3; 225 in FIG. 4). For example, purification/enhancement unit 25 may comprise a hydrogen separation unit, and hydrogen separated therein may be introduced via component outlet line 30 and hydrogen inlet line 75 into product upgrading unit(s) 80. (In such an instance, line 30 and 75 may comprise a single line).

In some embodiments, upgrading at least a portion of the Fischer-Tropsch product into fuel comprises hydrogenation and the method further comprises removing hydrogen from the alcohol-derived synthesis gas in line 20 (120 in FIG. 3; 220 in FIG. 4), from the synthesis gas in line 120a or line 120b of FIG. 3, from synthesis gas in lines 220a or 220b of FIG. 4, or from any combination thereof prior to introducing the synthesis gas into the Fischer-Tropsch reactor. In applications, at least a portion of the recovered hydrogen is utilized for product upgrading, e.g. hydrogenation, by introduction of the recovered hydrogen into a product upgrading unit.

In embodiments, the fuel production method provides a diesel fuel additive. For example, in embodiments, Fischer-Tropsch product formed from a synthesis gas stream, at least a part of which is derived from alcohol, is upgraded by separation of desired boiling fractions (e.g., diesel boiling fractions), isomerization, and/or blending of various fractions.

The Fischer-Tropsch synthesis of hydrocarbonaceous products may provide a significant quantity of by-product naphthas. Product upgrading may comprise processing these light Fischer-Tropsch naphthas to increase the production of middle distillate Fischer-Tropsch fuels.

It is known that the primary cause of particulate matter emission is incomplete combustion of the fuel and attempts have been made to introduce into the fuel organic compounds which have oxygen value therein (hereafter referred to as "oxygenates") to facilitate combustion. Oxygenates are known to facilitate the combustion of fuel to reduce the particulate matter. Examples of such compounds include some of the lower aliphatic esters such as, e.g., the ortho esters of formic and acetic acid, ethers, glycols, polyoxyalkylene glycols, ethers and esters of glycerol, and carbonic acid esters. In embodiments, upgrading of Fischer-Tropsch product to fuel or fuel component comprises adding at least one such component to the fuel. In embodiments, the added component is capable of reducing particulate emissions from the exhausts of engines which generate power by combustion of such fuels.

In embodiments, upgrading the product comprises adding ethers to the fuel. In applications, ethers and/or alkyl or dialkyl peroxides are blended with Fischer Tropsch diesel fuel product. Without wishing to be limited by theory, the ether may provide a cleaner burning fuel with significantly decreased hydrocarbon, carbon monoxide and/or particulate matter emissions. Such supplements may enhance the cetane number of the fuel and impart other desirable properties to the fuel, such as reduced pour and cloud points.

In embodiments, the fuel produced via the disclosed fuel production process I is selected from aviation-grade fuel, aviation-grade fuel components, diesel fuel, diesel fuel components and combinations thereof. In embodiments, the process provides a fuel that has a high cetane number, combusts to produce a low level of NOx and/or a low level of particulate matter, PM, and/or comprises a low level of sulfur.

Figure 2:
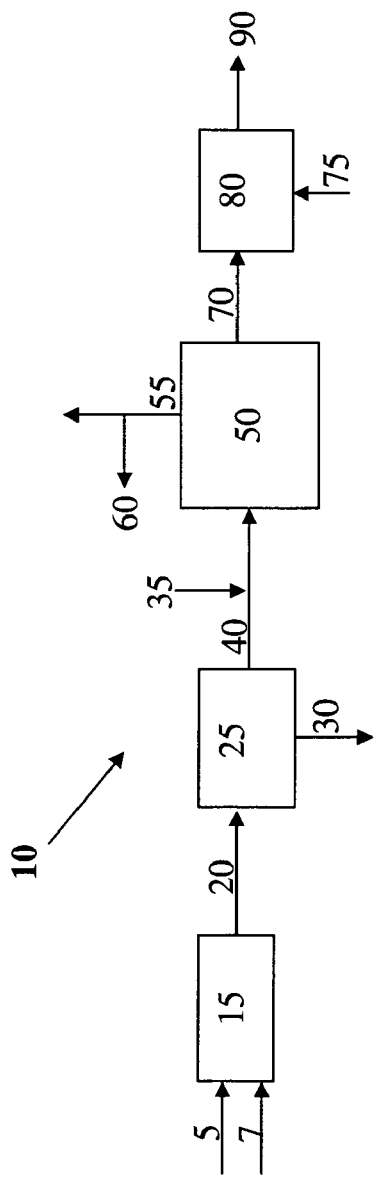
FIG. 2 is a schematic of a system suitable for carrying out a process for the production of Fischer-Tropsch fuel from alcohol-derived synthesis gas according to an embodiment of this invention.

In embodiments, the fuel in line 90 of the embodiment of FIG. 2 (line 190 in FIG. 3; line 290 in FIG. 4) comprises substantially no sulfur. In embodiments, the fuel produced by the method of this disclosure comprises less sulfur than ultra low sulfur (petroleum) diesel, ULSD. In embodiments, the fuel comprises less than 500 ppm sulfur, less than 15 ppm sulfur, less than 10 ppm sulfur, less than 5 ppm sulfur, less than 3 ppm sulfur, or less than 1 ppm sulfur.

In embodiments, fuel produced by the disclosed method combusts to yield a NOx level equal to or less than that produced by combustion of ULSD. In embodiments, the fuel produces less than about 1 g/tonne-kg NOx upon combustion.

In embodiments, the fuel produced via the disclosed system and method produces the same amount or less particulate matter, PM 10, than ULSD upon combustion. In embodiments, the fuel produces less than about 60, 50, 40 or 30 mg/tonne-km PM10 upon combustion.

In embodiments, the fuel produced by the disclosed system and method has a high cetane number. In embodiments, the fuel has a cetane number of greater than about 30, greater than about 40, or greater than about 50.

While the preferred embodiments of the invention have been shown and described, modifications thereof can be made by one skilled in the art without departing from the spirit and teachings of the invention. The embodiments described herein are exemplary only, and are not intended to be limiting. Many variations and modifications of the invention disclosed herein are possible and are within the scope of the invention. Accordingly, the scope of protection is not limited by the representative description set out above, but is only limited by the claims which follow, that scope including all equivalents of the subject matter of the claims.

The disclosures of all patents, patent applications, and publications cited herein are hereby incorporated herein by reference in their entirety, to the extent that they provide exemplary, procedural, or other details supplementary to those set forth herein.

What is claimed is:

1. A method of producing fuel, the method comprising:
   converting an alcohol stream comprising at least one alcohol into synthesis gas;
   providing a first synthesis gas stream, wherein at least a portion of the first synthesis gas stream comprises synthesis gas obtained from the alcohol conversion;
   converting a feed comprising synthesis gas via Fischer-Tropsch into a Fischer-Tropsch product comprising hydrocarbons, wherein at least a portion of the feed comprises synthesis gas from the first synthesis gas stream, and wherein the feed further comprises non-alcohol derived synthesis gas; and
   converting at least a portion of the Fischer-Tropsch product into fuel.

2. The method of claim 1 wherein the at least one alcohol is derived from corn, sugar cane, biomass, lignocellulose, cellulose, coal, natural gas, or a combination thereof.

3. The method of claim 1 wherein the at least one alcohol comprises ethanol.

4. The method of claim 3 wherein the ethanol is derived from lignocellulose, cellulose, or a combination thereof.

5. The method of claim 3 wherein at least a portion of the ethanol is derived from fermentation of sugar cane, fermentation of corn, thermochemical conversion of synthesis gas or a combination thereof.

6. The method of claim 3 wherein converting an alcohol stream comprising at least one alcohol into synthesis gas comprises converting ethanol to synthesis gas by reforming, partial oxidation, gasification, or a combination thereof.

7. The method of claim 1 further comprising producing the non-alcohol derived synthesis gas via at least one process selected from gasification of coal, gasification of biomass, reforming of natural gas, and combinations thereof.

8. The method of claim 1 wherein the at least one alcohol is ethanol, and wherein converting the alcohol stream into synthesis gas comprises gasifying the alcohol stream to produce a gasifier product comprising synthesis gas having a first $H_2$:CO ratio.

9. The method of claim 8 further comprising combining the gasifier product with the non-alcohol derived synthesis gas to yield the first synthesis gas stream, wherein the first synthesis gas stream has a second $H_2$:CO ratio.

10. The method of claim 9 wherein the second $H_2$:CO ratio is greater than the first $H_2$:CO ratio.

11. The method of claim 9 wherein the second $H_2$:CO ratio is less than the first $H_2$:CO ratio.

12. The method of claim 9 wherein the non-alcohol derived synthesis gas is obtained from at least one process selected from gasification of coal, gasification of biomass, reforming of natural gas, and combinations thereof.

13. The method of claim 8 further comprising gasifying at least one selected from liquid hydrocarbons, coal, biomass, petcoke and combinations thereof to provide the non-alcohol derived synthesis gas.

14. The method of claim 8 further comprising shifting the gasifier product via water gas shift reaction whereby water and a portion of the carbon monoxide in the gasifier product are converted into additional hydrogen and carbon dioxide, whereby a water gas shift product having a second $H_2$:CO ratio is obtained, wherein the second $H_2$:CO ratio is greater than the first $H_2$:CO ratio.

15. The method of claim 1 wherein the at least one alcohol comprises ethanol and wherein converting the alcohol stream into synthesis gas comprises reforming the alcohol stream.

16. The method of claim 15 wherein reforming comprises autothermal reforming.

17. The method of claim 15 further comprising reforming natural gas to provide the non-alcohol derived synthesis gas.

18. The method of claim 1 further comprising removing at least one component from the first synthesis gas stream prior to utilization of the at least a portion thereof in the feed gas.

19. The method of claim 18 wherein the at least one component is selected from the group consisting of sulfur, carbon dioxide, halides, sulfur-containing compounds, hydrogen, and combinations thereof.

20. The method of claim 19 wherein the at least one component is hydrogen, wherein converting at least a portion of the Fischer-Tropsch product into fuel comprises upgrading at least a portion of the Fischer-Tropsch product via hydrogenation, and wherein at least a portion of the removed hydrogen is utilized to hydrogenate the Fischer-Tropsch product.

21. The method of claim 1 wherein the fuel is selected from aviation-grade fuels, aviation-grade fuel components, diesel fuels, diesel fuel components, and combinations thereof.

22. The method of claim 1 wherein the fuel has a sulfur level less than that of ultra low sulfur diesel.

23. The method of claim 1 wherein, upon combustion, the fuel produces NOx emissions at a level at least as low as that of ultra low sulfur diesel.

24. The method of claim 1 wherein, upon combustion, the fuel produces PM10 at least as low as ultra low sulfur diesel.

25. The method of claim 1 wherein the fuel has a cetane number of greater than about 40.

26. A method of producing a diesel fuel, the method comprising forming hydrocarbons via Fischer-Tropsch conversion of alcohol-derived and non-alcohol derived synthesis gas, optionally upgrading at least a portion of the hydrocarbons to provide hydrocarbons boiling in the diesel range, and utilizing at least a portion of the Fischer-Tropsch hydrocarbons, at least a portion of the upgraded hydrocarbons, or both as a diesel fuel or as a component of a diesel fuel.

27. The method of claim 26 further comprising producing at least a portion of synthesis gas via reforming of ethanol.

* * * * *